United States Patent
Dixon

(10) Patent No.: US 7,712,474 B2
(45) Date of Patent: May 11, 2010

(54) STATIONARY AND WATERPROOF EXFOLIATING DEVICE

(76) Inventor: Laura Dixon, 7151 Gaston Ave., #803, Dallas, TX (US) 75214

( * ) Notice: Subject to any disclaimer, the term of this patent is extended or adjusted under 35 U.S.C. 154(b) by 512 days.

(21) Appl. No.: 11/491,559

(22) Filed: Jul. 24, 2006

(65) Prior Publication Data

US 2008/0045974 A1 Feb. 21, 2008

(51) Int. Cl.
*A45D 29/18* (2006.01)
(52) U.S. Cl. .................... 132/76.4; 132/75.6
(58) Field of Classification Search ............... 132/76.4, 132/75.6, 73, 73.5; 601/136, 134, 137, 138; 15/104.92, 218; 451/523, 524, 525, 539, 451/538
See application file for complete search history.

(56) References Cited

U.S. PATENT DOCUMENTS

| | | | | |
|---|---|---|---|---|
| 3,192,678 A | * | 7/1965 | Buratti | 451/522 |
| D297,376 S | * | 8/1988 | Bastedo | D28/63 |
| D326,931 S | * | 6/1992 | Tomsick | D28/63 |
| 5,621,986 A | | 4/1997 | Medina et al. | |
| D388,547 S | * | 12/1997 | Walls | D28/63 |
| 5,913,313 A | | 6/1999 | Brunderman | |
| 6,053,464 A | * | 4/2000 | Cardarelli | 248/205.8 |
| 6,142,156 A | | 11/2000 | Brunderman | |
| 6,210,350 B1 | * | 4/2001 | Finch | 601/136 |
| 6,530,096 B1 | | 3/2003 | Mayhew et al. | |
| 6,662,398 B1 | * | 12/2003 | Thomson | 15/104.92 |
| 6,740,052 B1 | * | 5/2004 | Regner | 601/136 |
| 6,779,218 B1 | | 8/2004 | Jusinski | |

OTHER PUBLICATIONS

WO 2005/020775 A1 Minchinton-Brown, Epidermal Exfoliator Mar. 10, 2005.*

* cited by examiner

*Primary Examiner*—Robyn Doan
(74) *Attorney, Agent, or Firm*—John G. Fischer, Esq.; Storm LLP

(57) ABSTRACT

A disposable device for exfoliating skin is disclosed which is simple and inexpensive to manufacture. The device can be secured to a shower floor or wall without tools or adhesives, and provides a stationary and waterproof exfoliating device for hands-free use while showering.

8 Claims, 3 Drawing Sheets

STATIONARY AND WATERPROOF EXFOLIATING DEVICE

CROSS REFERENCE TO RELATED APPLICATIONS

None.

BACKGROUND OF THE INVENTION

1. Field of the Invention

The present invention relates to a disposable device for exfoliating skin and, in particular, to a simple and inexpensive device that can be secured to a shower floor or wall without tools or adhesives, and which provides a stationary and waterproof exfoliating surface for hands-free use while showering.

2. Description of the Related Art

In the normal course of personal health care, exfoliation of the skin is common practice. Exfoliation is the action of scrubbing skin with a gritty substance to remove the dead skin from the surface. In particular, it is common practice to exfoliate the feet. As with the feet, exfoliation can be practiced to remove calluses and corns.

One option for treatment is to visit a doctor, foot care specialist, or salon. Each of these options requires time, cost, and the added inconvenience to make appointments and travel there and back. While salons are far more convenient and affordable than an appointment with a medical specialist, recent information regarding exposure to harmful bacteria and viruses in these environments has decreased their appeal. Most people desire to have the capability of exfoliating their skin themselves, in the privacy of their home.

Most exfoliating devices are handheld devices that require the user to sit down or balance on one foot to exfoliate each foot with a pumice stone or other equally abrasive surface. The disadvantage of this method is that dry skin is then dispersed onto the floor, requiring clean-up. Another disadvantage, particularly for large or elderly persons, is that the position required to reach the lowest extremities of the body is uncomfortable. Another disadvantage is that persons with physical disabilities, such as arthritis, find it painful to exfoliate the feet in this position. Another disadvantage is that in this position, the arms can get tired from scrubbing. Another disadvantage is that dry skin is more difficult to exfoliate.

The most convenient location in the home for people to exfoliate their feet is in the shower or bathtub. Exfoliated skin is very small and easily dispensed down the drain. However, large or elderly people may have physical difficulty exfoliating their feet in a shower, and doing so without risking loss of balance and serious injury from falling.

To resolve this problem, devices have been developed which are secured to the floor of the shower, allowing persons to exfoliate their feet hands-free, and without bending over uncomfortably. They can then use their hands to support themselves in the shower while using the strength of their lower body to exfoliate each foot. Devices such as these typically incorporate a pumice stone secured to an elastic base having suction cups beneath the base.

U.S. Pat. No. 6,530,096, issued to Mayhew et al., claims a method for exfoliation. Disclosed is a large, generally flat rubber pad having multiple suction cups on the bottom and an abrasive surface on the top.

U.S. Pat. No. 6,210,350, issued to Finch, discloses a contoured exfoliating device for use in the shower, having a Scotch Brite® abrading surface which includes a flexible matted type layer, and having flexible sidewalls.

U.S. Pat. Nos. 5,913,313 and 6,142,156, issued to Brunderman, disclose exfoliating products of pumice stone including a separate toe stick for exfoliation between the toes, and particular geometric configurations of the pumice to more comfortably access certain areas of the foot.

U.S. Pat. No. 6,779,218, issued to Jusinski, discloses an exfoliating device configured to fit in a corner of a shower, and capable of supporting a scraping device, a soaping device, and a brushing device.

U.S. Pat. No. 5,621,986, issued to Medina et al., discloses a slipper device having a pumice stone attached to a top surface of the slipper such that one can rub the other bare foot on the stone.

A principal disadvantage of these prior art devices is that most of them rely upon the use of a pumice stone. Pumice stones are hard and inflexible, requiring the person's foot to conform to the stone to perform exfoliation. This requires extensive and particular positioning of the foot against the stone to comfortably exfoliate the desired portion of the foot.

A second disadvantage is that accidental contact with the stone in the shower can be frequent and painful, as people are not normally inclined to look downward when moving around under the water flow of a shower. A third disadvantage of these devices is that when left in a moist environment, like a shower, the permeable pumice stone will experience mold growth. Mold is unsightly, unhealthy, and potentially hazardous.

A fourth disadvantage of these devices is that they are relatively expensive and therefore not disposable. This disadvantage is magnified by the potential for mold growth, such that discarding the device is often required before the stone has reached the end of its useful life. The products should be cleaned and disinfected on a regular basis for extended, continued use.

A fifth disadvantage is that devices using interwoven plastics, such as Scotch Brite®, retain unsightly exfoliated material within the matted structure, which can provide a nutrient source for microbial growth. A sixth disadvantage of these devices is that they take up too much room in the shower.

A seventh disadvantage of the known devices is that they are heavy, generally exceeding 4 ounces in weight, such that they are expensive to ship, and too heavy to be suspended in a vertical position against a shower wall without falling off over time.

Therefore, there is a need to develop an improved exfoliating device that is disposable, capable of being attached to a shower floor, having a lightweight, deformable structure with an abrasive texture adhered with a waterproof and flexible adhesive, being resistant to mold growth, and being cost effective to replace.

SUMMARY OF THE INVENTION

Unique to this invention, the exfoliating device has a body that is both the attachment device and the exfoliating device. A primary advantage of the preferred embodiment of the present invention is that it does not incorporate a solid pumice stone. The device is deformable and permits the device to partially conform to the foot being exfoliated without extensive and particular positioning of the foot in relation to the device.

A second advantage of the present invention is that, due to its small size and deformable surface, accidental contact with the device is less likely and, therefore, less harmful. A third advantage of the preferred embodiment is that it takes up less room on retail store shelves and in the shower. A fourth advantage of the present invention is that it is very inexpensive to manufacture, enabling the device to be a disposable product.

A fifth advantage of the present invention is that it is resistant to mold growth. A sixth advantage of the present invention is that it does not accumulate exfoliated material. A seventh advantage of the present invention is that it is very lightweight.

As referred to hereinabove, the "present invention" refers to one or more embodiments of the present invention which may or may not be claimed, and such references are not intended to limit the language of the claims, or to be used to construe the claims in a limiting manner.

The present invention relates to a device for exfoliating feet, having a hollow body formed of a compressible, water-resistant, elastomeric material. In the preferred embodiment, the interior of the body is substantially parallel to the interior surface. A substantially flat base connects the interior and exterior surfaces. The exterior surface is textured. An abrasive material is adhered to the exterior surface with an adhesive. When some of the air is evacuated from the interior of the body, the base forms a suction seal with an attaching surface, such as a shower floor.

In another preferred embodiment, the body has a hemispherical shape. In another preferred embodiment, the diameter of the body is between approximately 2 and 4 inches. In a more preferred embodiment, the diameter of the body is approximately 2.25 inches.

In another preferred embodiment, the base is chamfered at a radial angle having a center located on the centerline of the hemispherical body. In another preferred embodiment, the radial angle formed is between approximately 1 and 10 degrees above the center of the body.

In another preferred embodiment, the base has a thickness of between 0.2 and 0.3 inches. In the preferred embodiment, the body is made of a water-resistant, elastomeric material having a Shore A Durometer hardness of between 55-60.

In another preferred embodiment, a method of manufacturing the exfoliating device is disclosed, comprising the steps of:

1. abrading a hemispherical body;
2. applying a waterproof adhesive to the exterior of the body; and,
3. coating the exterior of the body with a granular abrasive material.

In another preferred embodiment, the body is a suction cup formed of a compressible, water-resistant, elastomeric material. The cup has an exterior surface with an abrasive material adhered to it.

BRIEF DESCRIPTION OF THE DRAWINGS

The objects and features of the invention will become more readily understood from the following detailed description and appended claims when read in conjunction with the accompanying drawings in which like numerals represent like elements.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Figure 1:
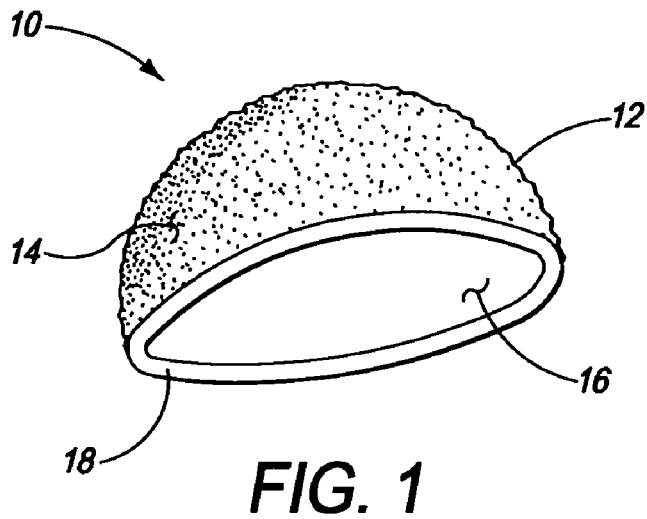
FIG. 1 is an isometric view of an exfoliating device made in accordance with a preferred embodiment of the present invention.

FIG. 1 is an isometric view of an exfoliating device 10, illustrated in accordance with a preferred embodiment of the present invention. Exfoliating device 10 has a hollow body 12. Body 12 has an exterior surface 14 and a substantially parallel interior surface 16. In the preferred embodiment, exterior surface 14 is textured, so that it is not smooth.

Exterior 14 and interior 16 are connected by a substantially flat base 18. In the preferred embodiment, hollow body 12 is formed of a compressible, water-resistant, elastomeric material.

Figure 2:
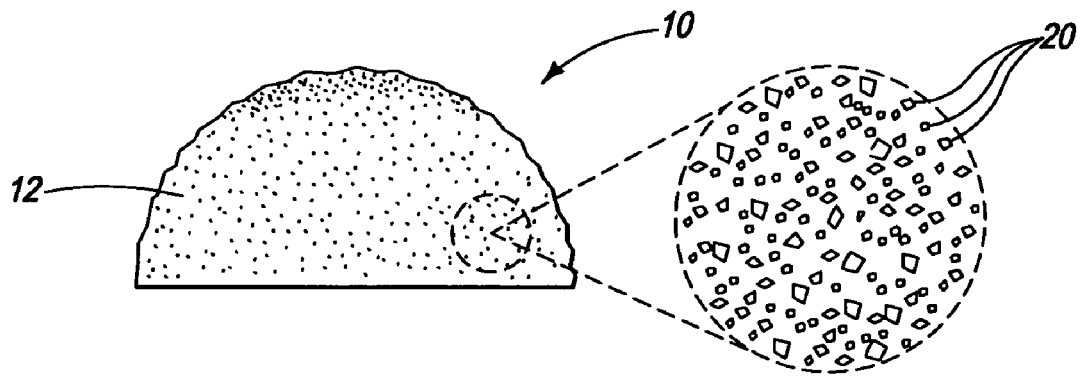
FIG. 2 is a side view of the exfoliating device disclosed in FIG. 1.

FIG. 2 is a side view of exfoliating device 10. As illustrated in the break-out of this view, an abrasive material 20 is adhered to exterior 14 of body 12. Abrasive material 20 is preferably adhered with an adhesive, such as a modified silicone adhesive. In a more preferred embodiment, abrasive material 20 is comprised of particles of various sizes, providing a non-homogeneous surface. In a preferred embodiment, abrasive material 20 is a granular abrasive having a Phi scale measurement of between 7 and −1.

In another preferred embodiment, body 12 is hemispherical in shape. Preferably, body 12 has a diameter of between 2 and 4 inches. In a more preferred embodiment, body 12 has a diameter of approximately 2.25 inches. In another preferred embodiment, body 12 has a Shore A Durometer hardness of between 55-60.

Figure 3:
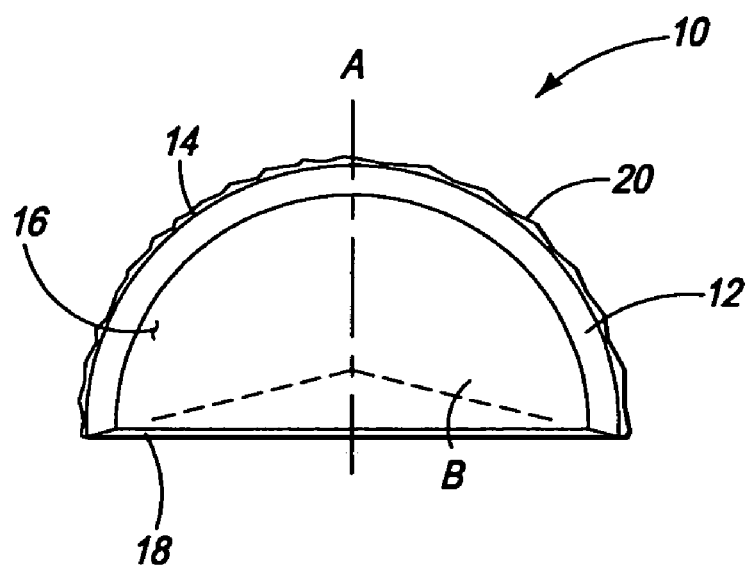
FIG. 3 is a side-sectional view of an exfoliating device made in accordance with another preferred embodiment of the present invention

FIG. 3 is a side-sectional view of an alternative embodiment of exfoliating device 10. In this embodiment, base 18 is disposed at an angle β relative to the diameter of body 12. In the preferred embodiment, angle β is between approximately 1 and 10 degrees.

Figure 4:
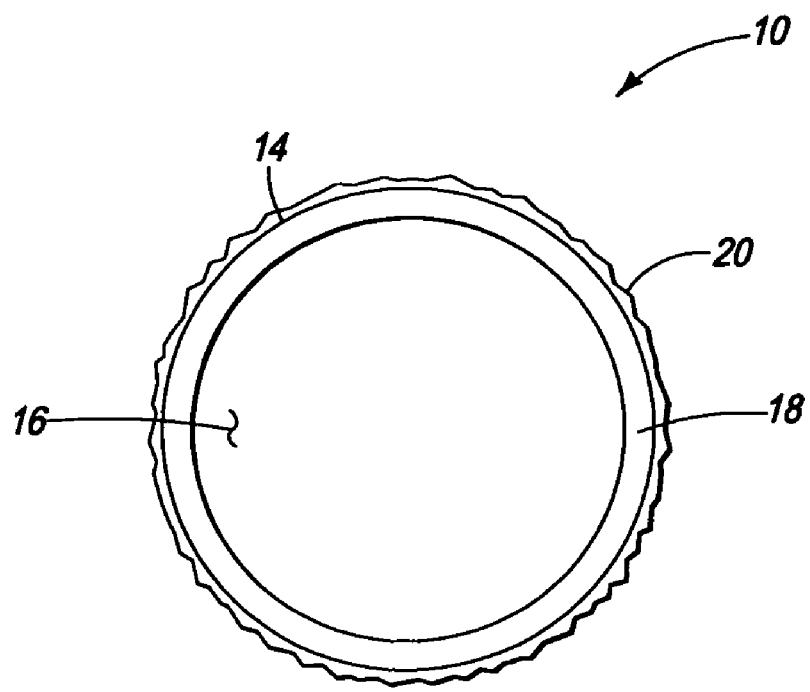
FIG. 4 is a bottom view of the exfoliating device disclosed in FIGS. 1 and 2.

FIG. 4 is a bottom view of exfoliating device 10. In this view, it can be seen that abrasive material 20 is not adhered to base 18. Base 18 is smooth to permit an airtight seal with an attaching surface when at least some air is evacuated from the inside of body 12. In the preferred embodiment, base 18 has a thickness of between 0.2 and 0.3 inches.

In an alternative embodiment, a method of manufacturing is disclosed, comprising the steps of:

1. abrading a hemispherical body;
2. applying a waterproof adhesive to the exterior of the body; and,
3. coating the exterior of the body with a granular abrasive material.

OPERATION OF THE INVENTION

The present invention discloses a novel exfoliating device that is small, lightweight, inexpensive, waterproof, and disposable. In the preferred embodiment, exfoliating device 10 has a hollow body 12. Body 12 has an exterior surface 14 and a substantially parallel interior surface 16. Exterior 14 and interior 16 are connected by a substantially flat base 18. Body 12 is formed of a compressible, water-resistant, elastomeric material.

Unique to this invention, exfoliating device 10 has a body 12 that is both the attachment device and the exfoliating device. Interior 16 forms the cavity for creating a suction force. Exterior 18 is deformable, and has an abrasive material such as sand adhered thereto to form the exfoliating surface. Many advantages are obtained from this design. Among the advantages, it is small, disposable, capable of being attached to a shower floor or wall, lightweight, deformable, and resistant to mold growth.

In the preferred embodiment, exterior surface 14 is textured, so that it is not smooth. Texturing of exterior surface 14 is preferably accomplished by abrading the material, such as by grinding. A grinding wheel type that is satisfactory for this purpose is a resin-bonded bubble alumina wheel. Texturing exterior surface 14 provides a superior adherence of abrasive material 20.

As illustrated in the break-out of FIG. 2, abrasive material 20 is adhered to exterior 14 of body 12 by means of an adhesive. Experimentation has demonstrated that adhesives that satisfy this purpose are commercially available, such as, for example, Craft Bond Stix All™ manufactured by Elmer's Products, Inc., 180 E. Broad St., Columbus, Ohio 43215.

Abrasive material 20 may be comprised of particles of various sizes, providing a non-homogeneous exfoliating surface for improved exfoliation. A non-homogeneous distribution of abrasive material 20 on exterior 14 prevents clogging with exfoliated waste. Alternatively, a narrower distribution of abrasive material 20 can provide a user's preferred abrasiveness. In the preferred embodiment, abrasive material 20 is a granular abrasive having a Phi scale measurement of between 7 and −1.

In the preferred embodiment, body 12 is hemispherical in shape. Preferably, body 12 has a diameter of between 2 and 4 inches. Also, preferably, body 12 and base 18 have a thickness of between 0.2 and 0.3 inches. In a preferred embodiment, body 12 has a Shore A Durometer hardness of between approximately 55-60. These features provide a balance between deformation for evacuation and attachment, and still provide a substantially rigid structure necessary for exfoliating activity.

Base 18 is preferably non-textured (generally smooth) and free of abrasive material 20 to permit an airtight seal with an attaching surface when at least some air is evacuated from the inside of body 12. In the preferred embodiment, base 18 has a thickness of between 0.2 and 0.3 inches.

In the alternative embodiment illustrated in FIG. 3, base 18 is disposed at an angle β relative to the diameter of body 12. In the preferred embodiment, angle β is between approximately 1 to 10 degrees. Depending on the geometrical configuration of body 12, this feature may enhance attachment of device 10 to a surface, such as a floor, by increasing the contact area of base 18 with the intended attachment surface. This occurs as a result of expansion of base 18 during compression of body 12 to partially evacuate the air from the interior of the device 10.

In an alternative embodiment, a method of manufacturing is disclosed, comprising the steps of:
1. abrading a hemispherical body;
2. applying a waterproof adhesive to the exterior of the body; and,
3. coating the exterior of the body with a granular abrasive material.

Figure 5:
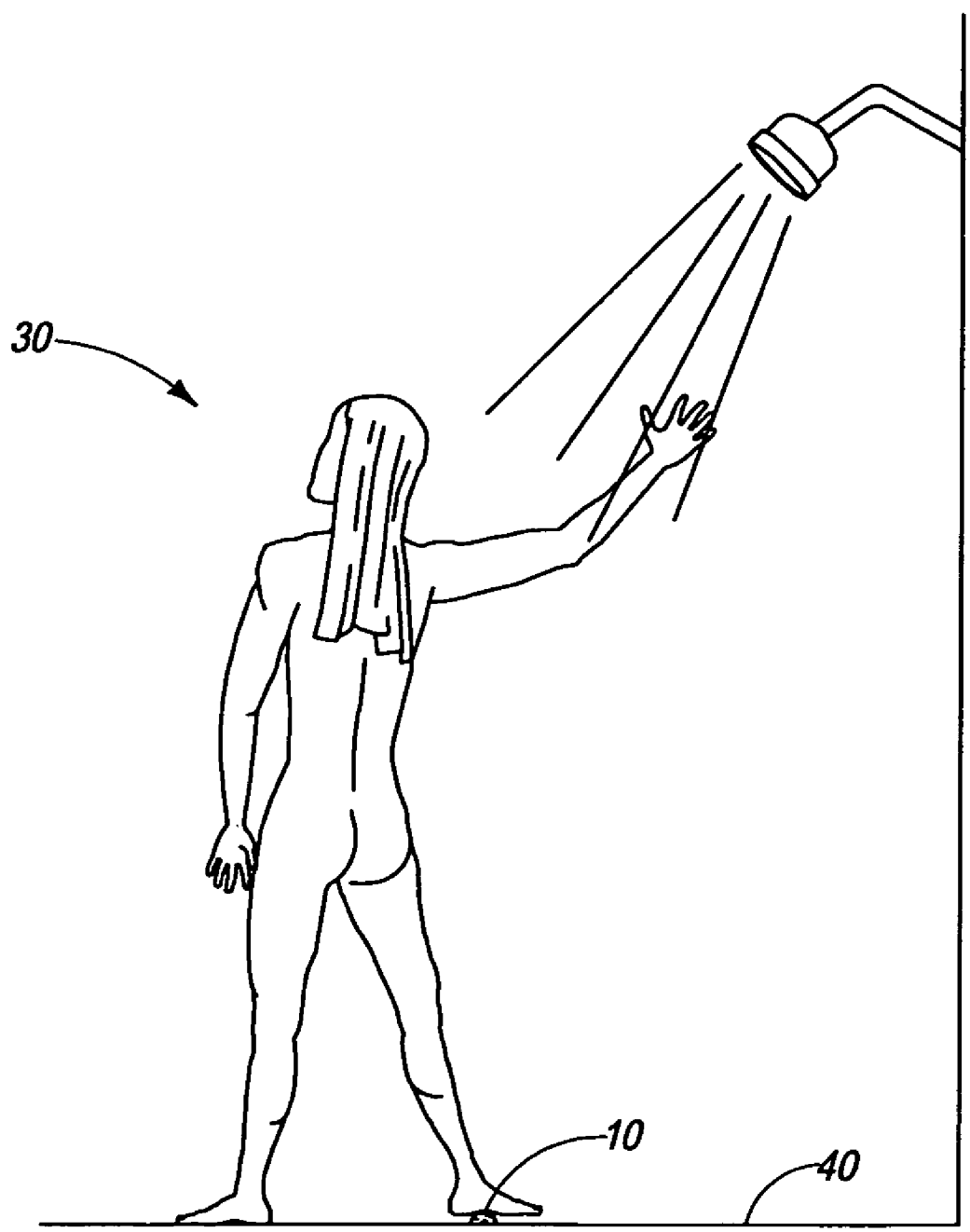
FIG. 5 is a side view of a preferred embodiment, the exfoliating device shown being used in the recommended manner, as attached to a shower floor.

FIG. 5 is a side view of exfoliating device 10 shown being used in the recommended manner, as attached to a shower floor 40. In this view, it is seen that exfoliating device 10 takes up very little room in the shower 40. The user 30 has her hands free to optionally stabilize herself against the shower wall 40, as shown. Although FIG. 5 illustrates attachment of exfoliating device 10 to a shower floor 40, exfoliating device 10 can be readily attached to a shower wall, counter top, or other surface. Exfoliating device 10 can also be handheld during exfoliation. Exfoliating device 10 is thus not limited to use for exfoliation of the feet, but can be used to exfoliate all bodily skin.

As a benefit of its inexpensive construction, device 10 provides a truly disposable option for a foot exfoliating device. As with any product associated with biological material, use between individuals is not recommended. Thus, the present invention provides an affordable option for hotels and resorts, as well as for home use.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of preferred embodiments. Accordingly, it is appropriate that the appended claims be construed broadly and in a manner consistent with the scope of the invention.

I claim:

1. An apparatus for exfoliating feet, comprising:
   a hemispherical hollow body formed of a compressible, water-resistant, elastomeric material;
   the body having an interior surface, an exterior surface substantially parallel to the interior surface, and a substantially flat base connecting the interior and exterior surfaces;
   an abrasive material adhered to the exterior surface with an adhesive, said abrasive material is an granular abrasive having a Phi scale measurement of between 7 and −1; and wherein the base is configured to be in direct contact with an attaching surface to form an airtight seal with the attaching surface when at least some air is evacuated from the inside of the body.

2. The device of claim 1, wherein the adhesive being a silicon based adhesive.

3. The device of claim 1, further comprising:
   wherein the base has a thickness of between approximately 0.2 and 0.3 inches.

4. The device of claim 1, further comprising:
   wherein the body is made of a water-resistant, elastomeric material having a Shore A Durometer hardness of between approximately 55-60.

5. The device of claim 1, further comprising:
   wherein the body has a diameter of between 2 and 4 inches.

6. The device of claim 1, further comprising:
   wherein the body has a diameter of approximately 2.25 inches.

7. The device of claim 1, further comprising:
   wherein the base is disposed at a radial angle having a center located within the body.

8. The device of claim 7, further comprising:
   wherein the radial angle formed is between approximately 1 and 10 degrees.

* * * * *